(12) United States Patent
Grace (10) Patent No.: US 10,864,370 B2
(45) Date of Patent: *Dec. 15, 2020

(54) MULTI-LOOP COUPLING FOR LEAD EXTENSION AND EXTRACTION

(71) Applicant: KONINKLIJKE PHILIPS N.V., Eindhoven (NL)

(72) Inventor: Kenneth P Grace, Woodland Park, CO (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 111 days.

This patent is subject to a terminal disclaimer.

(21) Appl. No.: 16/160,938

(22) Filed: Oct. 15, 2018

(65) Prior Publication Data

US 2019/0046788 A1    Feb. 14, 2019

Related U.S. Application Data

(63) Continuation of application No. 14/983,248, filed on Dec. 29, 2015, now Pat. No. 10,105,533.
(Continued)

(51) Int. Cl.
*A61B 17/221*   (2006.01)
*A61N 1/05*   (2006.01)
(Continued)

(52) U.S. Cl.
CPC ............ *A61N 1/056* (2013.01); *A61B 17/221* (2013.01); *A61B 17/32056* (2013.01);
(Continued)

(58) Field of Classification Search
CPC .............. A61B 17/00234; A61B 17/50; A61B 17/32056; A61B 17/221;
(Continued)

(56) References Cited

U.S. PATENT DOCUMENTS 1,891,497 A   12/1932   Birkenmaier
2,446,710 A    8/1948   Makaroff
(Continued)

FOREIGN PATENT DOCUMENTS

DE   19964093 B4   11/2001
EP     169784 A2    1/1986
(Continued)

OTHER PUBLICATIONS

Smith et al. Extraction of Transvenous Pacing and ICD Leads; Pace vol. 31 Jun. 2008 pp. 736-752.

*Primary Examiner* — Eugene T Wu (57) ABSTRACT

A device for extending a lead according to an embodiment of the present disclosure includes a body, wherein the body is elongated and includes at least two apertures; a first filament loop comprising a filament, the filament extending along the inner surface of the body and through at least one of the at least two apertures, the first filament loop extending outside the outer surface of the body; a second filament loop extending outside the outer surface of the body; the first and second filament loops arranged so as to receive therethrough a lead, the first and second filament loops being tightenable about the lead in a manner that grips the lead between the first and second filament loops and an outer surface of the lead; and a tether coupled to the lead via one or more of the body, the first filament loop, and the second filament loop.

13 Claims, 8 Drawing Sheets

Related U.S. Application Data (60) Provisional application No. 62/098,208, filed on Dec. 30, 2014.

(51) Int. Cl.
*A61B 17/3205* (2006.01)
*A61B 17/00* (2006.01)

(52) U.S. Cl.
CPC .............. *A61B 2017/00358* (2013.01); *A61B 2017/2212* (2013.01); *A61N 1/0587* (2013.01); *A61N 2001/0578* (2013.01)

(58) Field of Classification Search
CPC .. A61B 2017/00358; A61B 2017/2212; A61B 2017/2217; A61B 2018/1407; A61B 2018/141; A61M 25/01; A61N 2001/0578; A61N 2001/058
See application file for complete search history.

(56) References Cited

U.S. PATENT DOCUMENTS

| | | | |
|---|---|---|---|
| 2,615,402 A * | 10/1952 | Chamberlain, Jr. | B61B 12/127 104/202 |
| 2,627,137 A | 2/1953 | Koski | |
| 2,856,933 A | 10/1958 | Scharf et al. | |
| 3,068,608 A | 12/1962 | Counts | |
| 3,220,138 A | 11/1965 | Greenfield | |
| 3,955,578 A | 5/1976 | Chamness et al. | |
| 4,208,827 A | 6/1980 | Starkey | |
| 4,250,653 A | 2/1981 | Davies | |
| 4,471,777 A | 9/1984 | McCorkle, Jr. | |
| 4,506,471 A | 3/1985 | Riead | |
| 4,506,472 A | 3/1985 | Barman | |
| 4,582,056 A | 4/1986 | McCorkle et al. | |
| 4,636,346 A | 1/1987 | Gold et al. | |
| 4,824,435 A | 4/1989 | Giesy et al. | |
| 4,943,289 A | 7/1990 | Goode et al. | |
| 4,988,347 A | 1/1991 | Goode et al. | |
| 5,011,482 A | 4/1991 | Goode et al. | |
| 5,013,310 A | 5/1991 | Goode et al. | |
| 5,036,854 A | 8/1991 | Schollmeyer et al. | |
| 5,098,440 A | 3/1992 | Hillstead | |
| 5,163,938 A | 11/1992 | Kambara et al. | |
| 5,171,314 A | 12/1992 | Dulebohn | |
| 5,207,683 A | 5/1993 | Goode et al. | |
| 5,224,935 A | 7/1993 | Hollands | |
| 5,247,942 A | 9/1993 | Prather et al. | |
| 5,263,493 A | 11/1993 | Avitall | |
| 5,282,478 A | 2/1994 | Fleischhaker et al. | |
| 5,312,423 A | 5/1994 | Rosenbluth et al. | |
| 5,342,371 A * | 8/1994 | Welter | A61B 17/29 606/108 |
| 5,417,684 A | 5/1995 | Jackson et al. | |
| 5,443,472 A | 8/1995 | Li | |
| 5,509,902 A | 4/1996 | Raulerson | |
| 5,522,819 A | 6/1996 | Graves et al. | |
| 5,555,883 A | 9/1996 | Avitall | |
| 5,562,678 A | 10/1996 | Booker | |
| 5,611,803 A | 3/1997 | Heaven et al. | |
| 5,613,973 A | 3/1997 | Jackson et al. | |
| 5,632,749 A | 5/1997 | Goode et al. | |
| 5,637,098 A | 6/1997 | Bierman | |
| 5,653,716 A | 8/1997 | Malo et al. | |
| 5,681,347 A | 10/1997 | Cathcart et al. | |
| 5,693,059 A | 12/1997 | Yoon | |
| 5,697,936 A | 12/1997 | Shipko et al. | |
| 5,769,858 A | 6/1998 | Pearson et al. | |
| 5,782,839 A | 7/1998 | Hart et al. | |
| 5,823,971 A | 10/1998 | Robinson et al. | |
| 5,836,947 A | 11/1998 | Fleischman et al. | |
| 5,868,754 A | 2/1999 | Levine et al. | |
| 6,088,609 A | 7/2000 | Larison, II | |
| 6,090,129 A | 7/2000 | Ouchi | |
| 6,093,195 A | 7/2000 | Ouchi | |
| 6,136,005 A | 10/2000 | Goode et al. | |
| 6,167,315 A | 12/2000 | Coe et al. | |
| 6,290,693 B1 | 9/2001 | Jung et al. | |
| 6,375,639 B1 | 4/2002 | Duplessie et al. | |
| 6,432,115 B1 | 8/2002 | Mollenauer et al. | |
| 6,478,777 B1 | 11/2002 | Honeck et al. | |
| 6,500,182 B2 | 12/2002 | Foster | |
| 6,511,492 B1 | 1/2003 | Rosenbluth et al. | |
| 6,544,269 B2 | 4/2003 | Osborne et al. | |
| 6,575,988 B2 | 6/2003 | Rousseau | |
| 6,598,335 B2 | 7/2003 | Akhtar et al. | |
| 6,687,548 B2 | 2/2004 | Goode | |
| 6,695,813 B1 | 2/2004 | Boyle et al. | |
| 6,712,826 B2 | 3/2004 | Lui | |
| 6,743,228 B2 | 6/2004 | Lee et al. | |
| 6,840,000 B2 | 1/2005 | Akhtar et al. | |
| 6,893,450 B2 | 5/2005 | Foster | |
| 7,041,108 B2 | 5/2006 | Lippitt et al. | |
| 7,101,378 B2 | 9/2006 | Salameh et al. | |
| 7,210,210 B2 | 5/2007 | Lippitt et al. | |
| 7,359,756 B2 | 4/2008 | Goode | |
| 7,470,256 B2 | 12/2008 | Lampropoulos et al. | |
| 7,499,756 B2 | 3/2009 | Bowe et al. | |
| 7,520,881 B2 | 4/2009 | Foushee et al. | |
| 7,524,281 B2 | 4/2009 | Chu et al. | |
| 7,641,646 B2 | 1/2010 | Kennedy, II | |
| 7,651,503 B1 | 1/2010 | Coe et al. | |
| 7,651,504 B2 | 1/2010 | Goode et al. | |
| 7,713,275 B2 | 5/2010 | Greenberg et al. | |
| 7,727,253 B2 | 6/2010 | Ackerman et al. | |
| 7,731,693 B2 | 6/2010 | Melsheimer | |
| 7,753,917 B2 | 7/2010 | Urbanski et al. | |
| 7,753,918 B2 | 7/2010 | Hartley et al. | |
| 7,758,592 B2 | 7/2010 | Ayala et al. | |
| 7,776,052 B2 | 8/2010 | Greenberg et al. | |
| 7,824,342 B2 | 11/2010 | Minosawa et al. | |
| 7,871,414 B2 | 1/2011 | Hardin et al. | |
| 7,993,359 B1 | 8/2011 | Atwell et al. | |
| 8,070,693 B2 | 12/2011 | Ayala et al. | |
| 8,109,986 B2 | 2/2012 | Styrc | |
| 8,128,636 B2 | 3/2012 | Lui et al. | |
| 8,137,291 B2 | 3/2012 | Melsheimer | |
| 8,192,430 B2 | 6/2012 | Goode et al. | |
| 8,252,019 B2 | 8/2012 | Fleming et al. | |
| 8,323,179 B2 | 12/2012 | Chu et al. | |
| 8,326,437 B2 | 12/2012 | Cully et al. | |
| 8,469,970 B2 | 6/2013 | Diamant et al. | |
| 8,551,139 B2 | 10/2013 | Surti et al. | |
| 8,597,303 B2 | 12/2013 | Hammack et al. | |
| 8,702,625 B2 | 4/2014 | Ayala et al. | |
| 8,715,205 B2 | 5/2014 | Carter et al. | |
| 8,740,969 B2 | 6/2014 | Jensen et al. | |
| 8,747,295 B2 | 6/2014 | Chu et al. | |
| 8,758,326 B2 | 6/2014 | Hennessy | |
| 8,814,900 B2 | 8/2014 | Fleming et al. | |
| 9,220,523 B2 | 12/2015 | Taylor et al. | |
| 2002/0007204 A1 | 1/2002 | Goode | |
| 2002/0010475 A1 | 1/2002 | Lui | |
| 2002/0087100 A1 | 7/2002 | Onuki et al. | |
| 2002/0107526 A1 | 8/2002 | Greenberg et al. | |
| 2002/0123765 A1 | 9/2002 | Sepetka et al. | |
| 2004/0116939 A1 | 6/2004 | Goode | |
| 2004/0123765 A1 | 7/2004 | Furusawa et al. | |
| 2004/0153096 A1 | 8/2004 | Goode et al. | |
| 2004/0199200 A1 | 10/2004 | Teague et al. | |
| 2004/0243168 A1 | 12/2004 | Ferrera et al. | |
| 2005/0043743 A1 | 2/2005 | Dennis | |
| 2005/0096650 A1 | 5/2005 | Ouchi | |
| 2005/0177022 A1 | 8/2005 | Chu et al. | |
| 2005/0209609 A1 | 9/2005 | Wallace | |
| 2006/0073904 A1 | 4/2006 | Novak | |
| 2006/0100545 A1 | 5/2006 | Ayala et al. | |
| 2006/0149295 A1 | 7/2006 | Fleming, III | |
| 2007/0123804 A1 | 5/2007 | Ayala et al. | |
| 2007/0191919 A1 | 8/2007 | Lui et al. | |
| 2008/0147061 A1 | 6/2008 | Goode et al. | |
| 2008/0147111 A1 | 6/2008 | Johnson et al. | |
| 2008/0221587 A1 | 9/2008 | Schwartz | |

(56) References Cited

U.S. PATENT DOCUMENTS

| | | |
|---|---|---|
| 2009/0234367 A1 | 9/2009 | Verma |
| 2010/0042107 A1 | 2/2010 | Merrifield |
| 2010/0252049 A1 | 10/2010 | Kost |
| 2011/0106099 A1 | 5/2011 | Duffy et al. |
| 2011/0106107 A1 | 5/2011 | Binmoeller et al. |
| 2011/0112548 A1 | 5/2011 | Fifer et al. |
| 2011/0238078 A1 | 9/2011 | Goode et al. |
| 2012/0165827 A1 | 6/2012 | Khairkhahan et al. |
| 2012/0165850 A1 | 6/2012 | Deckard et al. |
| 2012/0310214 A1 | 12/2012 | Hennessy |
| 2013/0006261 A1 | 1/2013 | Lampropoulos et al. |
| 2013/0131688 A1 | 5/2013 | Schwartz |
| 2013/0172714 A1 | 7/2013 | Li et al. |
| 2013/0184738 A1 | 7/2013 | Laroya et al. |
| 2013/0184741 A1 | 7/2013 | Laroya et al. |
| 2013/0197476 A1 | 8/2013 | Karpiel |
| 2013/0238024 A1 | 9/2013 | Taylor et al. |
| 2013/0261638 A1 | 10/2013 | Diamant et al. |
| 2014/0155930 A1 | 6/2014 | Bennett et al. |
| 2014/0171960 A1 | 6/2014 | Goode et al. |
| 2014/0188124 A1 | 7/2014 | Lampropoulos et al. |
| 2014/0296905 A1 | 10/2014 | Dela |
| 2014/0350566 A1* | 11/2014 | Emmanouilidis ... A61B 17/1114 606/113 |
| 2014/0350593 A1 | 11/2014 | Laroya et al. |
| 2016/0183954 A1 | 6/2016 | Taylor et al. |
| 2016/0184576 A1 | 6/2016 | Grace et al. |
| 2016/0184579 A1 | 6/2016 | Triffo |

FOREIGN PATENT DOCUMENTS

| | | |
|---|---|---|
| EP | 0174930 A1 | 3/1986 |
| EP | 0368568 A1 | 5/1990 |
| EP | 0368568 B1 | 5/1990 |
| EP | 0661949 A1 | 7/1995 |
| EP | 0688184 A1 | 12/1995 |
| EP | 0708621 B1 | 5/1996 |
| EP | 0733382 A2 | 9/1996 |
| EP | 0733383 A2 | 9/1996 |
| EP | 1043042 B1 | 10/2000 |
| EP | 1063926 B1 | 1/2001 |
| EP | 1251787 B1 | 10/2002 |
| EP | 1284782 B1 | 2/2003 |
| EP | 1317214 B1 | 6/2003 |
| EP | 1330194 B1 | 7/2003 |
| EP | 1572282 B1 | 9/2005 |
| EP | 1587573 B1 | 10/2005 |
| EP | 1722696 A1 | 11/2006 |
| EP | 1757234 B1 | 2/2007 |
| EP | 1793886 B1 | 6/2007 |
| EP | 1815811 B1 | 8/2007 |
| EP | 1848497 B1 | 10/2007 |
| EP | 1951350 B1 | 8/2008 |
| EP | 1984056 A1 | 10/2008 |
| EP | 1984072 A2 | 10/2008 |
| EP | 1996089 B1 | 12/2008 |
| EP | 2054116 B1 | 5/2009 |
| EP | 2094178 B1 | 9/2009 |
| EP | 2124766 B1 | 12/2009 |
| EP | 2240126 B1 | 10/2010 |
| EP | 2349026 B1 | 8/2011 |
| EP | 2375997 B1 | 10/2011 |
| EP | 2489313 A1 | 8/2012 |
| EP | 2493392 B1 | 9/2012 |
| EP | 2496151 A2 | 9/2012 |
| EP | 2552327 A1 | 2/2013 |
| EP | 2659841 A2 | 11/2013 |
| EP | 2661233 A1 | 11/2013 |
| EP | 2661288 A1 | 11/2013 |
| EP | 2731513 A1 | 5/2014 |
| EP | 2740437 A1 | 6/2014 |
| EP | 2742871 B1 | 6/2014 |
| EP | 2783658 A2 | 10/2014 |
| EP | 2802276 A1 | 11/2014 |
| WO | 1996028101 A1 | 9/1996 |
| WO | 2001056484 A1 | 8/2001 |
| WO | 2001087412 A2 | 11/2001 |
| WO | 2002022028 A2 | 3/2002 |
| WO | 2005084563 A1 | 9/2005 |
| WO | 2007095252 A1 | 8/2007 |
| WO | 2007100474 A2 | 9/2007 |
| WO | 2008045143 A2 | 4/2008 |
| WO | 2008112608 A2 | 9/2008 |
| WO | 2010002549 A2 | 1/2010 |
| WO | 2011032157 A1 | 3/2011 |
| WO | 2011053645 A1 | 5/2011 |
| WO | 2011123342 A1 | 10/2011 |
| WO | 2012006247 A1 | 1/2012 |
| WO | 2013106713 A1 | 7/2013 |
| WO | 2014080338 A1 | 5/2014 |
| WO | 2014145598 A1 | 9/2014 |

* cited by examiner

MULTI-LOOP COUPLING FOR LEAD EXTENSION AND EXTRACTION

CROSS-REFERENCE TO RELATED APPLICATION

The present application is a Continuation of U.S. application Ser. No. 14/983,248, filed Dec. 29, 2015, entitled MULTI-LOOP COUPLING FOR LEAD EXTENSION AND EXTRACTION, which claims the benefit of and priority to, under 35 U.S.C. § 119(e), U.S. Provisional Application Ser. No. 62/098,208, filed Dec. 30, 2014, entitled MULTI-LOOP COUPLING FOR LEAD EXTENSION AND EXTRACTION, both of which are hereby incorporated by reference for their entirety for all purposes.

FIELD OF THE DISCLOSURE

The present disclosure relates generally to lead extension and extraction, and more specifically to methods and devices for extending a lead to lengthen a guide structure over which a lead extraction device may be passed.

BACKGROUND

Surgically implanted cardiac pacing systems, such as pacemakers and defibrillators, play an important role in the treatment of heart disease. In the 50 years since the first pacemaker was implanted, technology has improved dramatically, and these systems have saved or improved the quality of countless lives. Pacemakers treat slow heart rhythms by increasing the heart rate or by coordinating the heart's contraction for some heart failure patients. Implantable cardioverter-defibrillators stop dangerous rapid heart rhythms by delivering an electric shock.

Cardiac pacing systems typically include a timing device and a lead, which are placed inside the body of a patient. One part of the system is the pulse generator containing electric circuits and a battery, usually placed under the skin on the chest wall beneath the collarbone. To replace the battery, the pulse generator must be changed by a simple surgical procedure every 5 to 10 years. Another part of the system includes the wires, or leads, which run between the pulse generator and the heart. In a pacemaker, these leads allow the device to increase the heart rate by delivering small timed bursts of electric energy to make the heart beat according to a healthy rhythm. In a defibrillator, the lead has special coils to allow the device to deliver a high-energy shock and convert potentially dangerous rapid rhythms (ventricular tachycardia or fibrillation) back to a normal rhythm. Additionally, the leads may transmit information about the heart's electrical activity to the pacemaker.

For both of these functions, leads must be in contact with heart tissue. Most leads pass through a vein under the collarbone that connects to the right side of the heart (right atrium and right ventricle). In some cases, a lead is inserted through a vein and guided into a heart chamber where it is attached with the heart. In other instances, a lead is attached to the outside of the heart. To remain attached to the heart muscle, most leads have a fixation mechanism, such as a small screw and/or hooks at the end.

Within a relatively short time after a lead is implanted into the body, the body's natural healing process forms scar tissue along the lead and possibly at its tip, thereby fastening it even more securely in the patient's body. Leads usually last longer than device batteries, so leads are simply reconnected to each new pulse generator (battery) at the time of replacement. Although leads are designed to be implanted permanently in the body, occasionally these leads must be removed, or extracted. Leads may be removed from patients for numerous reasons, including but not limited to, infections, lead age, and lead malfunction.

Removal or extraction of the lead may be difficult. The body's natural healing process forms scar tissue over and along the lead, and possibly at its tip, thereby encasing at least a portion of the lead and fastening it even more securely in the patient's body. In addition, the lead and/or tissue may become attached to the vasculature wall. Both results may, therefore, increase the difficulty of removing the leads from the patient's vasculature. Typical leads in a human may pass through the innominate vein, past the superior vena cava ("SVC"), and into the right atrium of the heart. Tissue growth occurring along the SVC and other locations along the innominate vein may increase the risk and difficulty in extracting the leads from such locations, particularly when the vein(s)' walls are thin and the surrounding tissue is notably fibrous.

A variety of tools have been developed to make lead extraction safer and more successful. Current lead extraction techniques include mechanical traction, mechanical devices, and laser devices. Extracting a lead may often involve applying tension to the lead while it is still implanted, whether in order to pull it free using the tension force, to loosen it, and/or to apply an extraction device over the lead. Applying an extraction device over a lead which is not adequately tensioned may result in kinking or damage to the lead, for example at locations which are not as easy to access as the proximal portion of the lead that was near to or coupled with the pacemaker or defibrillator. In extracting a lead, the lead (including any conductive portions, insulating sheath, and/or casing layers) is often cut between the distal end of the lead and the proximal end of the lead (which is often coupled to the pacemaker). In other situations, the lead exhibits structural failure, either before, or during, the lead extraction surgical intervention. These situations may result in a lead that is not as long as the clinician would like it to be in order to both apply tension to the lead and/or deploy an extraction device over the lead. Existing lead extension technologies may be limited in the maximum level of tension which they can support in coupling with the lead, with the reversibility of such coupling, and/or with the reliability of such coupling.

SUMMARY

A device for extending a lead according to an embodiment of the present disclosure includes a body, wherein the body is elongated and includes at least two apertures formed through and between an inner surface and an outer surface of the body, a first filament loop comprising a filament, the filament extending along the inner surface of the body and through at least one of the at least two apertures, the first filament loop extending outside the outer surface of the body, a second filament loop extending outside the outer surface of the body, the first and second filament loops arranged so as to receive therethrough a lead, the first and second filament loops being tightenable about the lead in a manner that grips the lead between the first and second filament loops and an outer surface of the lead, and a tether coupled to the lead via one or more of the body, the first filament loop, and the second filament loop, the tether configured to extend further proximally than a proximal-most end of the lead, the tether further configured to transfer at least a portion of a tension force applied to the tether to the lead via the one or more of the body, the first filament loop, and the second filament loop.

A device wherein the filament is a first filament, and the second filament loop includes a second filament.

A device wherein the body is tubular and includes an opening at a distal end of the body, and the second filament loop extends through the opening.

A device wherein the first filament loop is tightenable independently of the second filament loop.

A device wherein the first and second filament loops both include and/or are formed by the filament, and the first and second filament loops are tightenable about the lead simultaneously upon application of tension to the filament.

A device wherein the device further includes a third filament loop extending outside the outer surface of the body, the first, second, and third filament loops being arranged so as to receive therethrough the lead, and the first, second, and third filament loops are tightenable about the lead in the manner that grips the lead between the first, second, and third filament loops and the outer surface of the lead.

A device wherein the filament is of a construct selected from the group consisting of monofilament wire, multifilament wire, monofilament suture, multifilament suture, and braided strands.

A device wherein each of the first and second filament loops may include, in some cases, at least a half twist outside the outer surface of the body.

A device wherein the filament is fixedly coupled to the body on one side of the first filament loop.

A method for extending a lead according to an embodiment of the present disclosure includes inserting a first filament loop and a second filament loop over a lead, the first and second filament loops extending outside an outer surface of a body, wherein the body is elongated and includes at least two apertures formed through and between an inner surface and the outer surface of the body, the first filament loop comprising a filament, the filament extending along the inner surface of the body and through at least one of the at least two apertures, the first filament loop extending outside the outer surface of the body; tightening the first and second filament loops about the lead in a manner that grips the lead between the first and second filament loops and an outer surface of the lead; and applying tension to the lead by applying tension to a tether that is coupled to the lead via the first and second filament loops when the first and second filament loops are tightened about the lead.

According to some embodiments of the present disclosure, tension may be applied to the tether by pulling the tether and/or a pull sleeve in a proximal direction relative to the body. According to some embodiments of the present disclosure, tension may be applied to the tether by holding the tether and/or the pull sleeve stationary and moving the body in a distal direction relative to the tether and/or the pull sleeve.

A method wherein tightening the first and second filament loops about the lead comprises applying tension to a pull loop extending proximally from the body and coupled to the first and second filament loops.

A method wherein tightening the first and second filament loops about the lead comprises applying tension to a sleeve translatably carried by the body and fixedly coupled to pull loop.

A method wherein tightening the first and second filament loops about the lead comprises applying tension to a sleeve translatably carried by the body and coupled to the first and second filament loops.

A method further comprising, prior to inserting the first filament loop and the second filament loop over the lead: coupling a device comprising the first filament loop, the second filament loop, and the body to a deployment sheath via the first and second filament loops; and deploying the device in a desired location by moving the deployment sheath to the desired location.

A method wherein coupling the device to the deployment sheath via the first and second filament loops comprises: inserting the first filament loop and the second filament loop over the deployment sheath; and tightening the first and second filament loops about the deployment sheath in a manner that grips the deployment sheath between the first and second filament loops and an outer surface of the deployment sheath.

A method further comprising, prior to inserting the first filament loop and the second filament loop over the lead, loosening the first filament loop and the second filament loop from the deployment sheath.

A method wherein tightening the first and second filament loops comprises: tightening the first filament loop about the lead; and independently tightening the second filament loop about the lead.

A method wherein the first and second filament loops both comprise the filament, and wherein tightening the first and second filament loops comprises applying tension to the filament to simultaneously tighten the first and second filament loops about the lead.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" may be used interchangeably herein. It is also to be noted that the terms "comprising", "including", and "having" may be used interchangeably.

A "lead" is a conductive structure, typically an electrically insulated coiled wire. The electrically conductive material may be any conductive material, with metals and intermetallic alloys common. The outer sheath of insulated material is biocompatible and bio stable (e.g., non-dissolving in the body) and generally includes organic materials such as polyurethane and polyimide. Lead types include, by way of non-limiting example, epicardial and endocardial leads. Leads are commonly implanted into a body percutaneously or surgically.

The term "means" as used herein shall be given its broadest possible interpretation in accordance with 35 U.S.C. Section 112(f). Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate possible and alternative examples of how the disclosure may be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Figure 1:
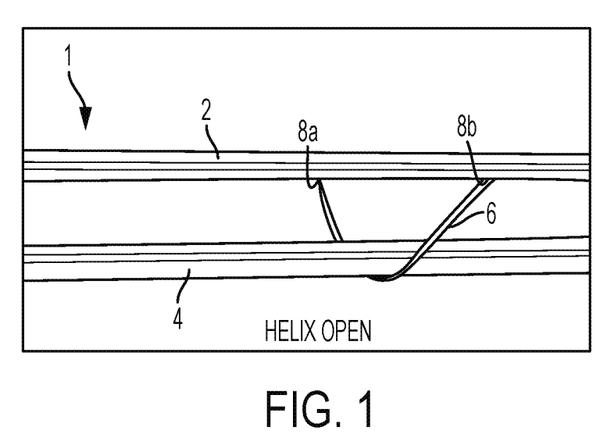
FIG. 1 illustrates a loop of a multi-loop lead extension device encircling a lead, according to an embodiment of the present disclosure.
Figure 2:
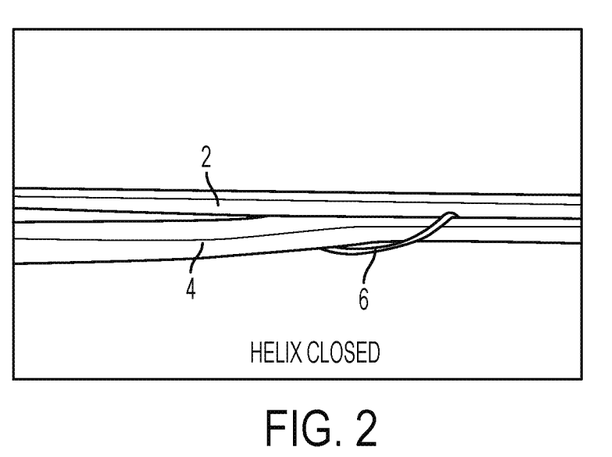
FIG. 2 illustrates the loop of FIG. 1 tightened about the lead, according to an embodiment of the present disclosure.

FIGS. 1 and 2 illustrates a loop 6 of a multi-loop lead extension device 1 encircling a lead 4, according to an embodiment of the present disclosure. The device 1 includes a body 2, which may be in the form of a hollow tube having an outer surface and an inner surface. The loop may be formed of a filament, for example a wire, and may extend through one or more apertures 8a, 8b formed in and through the body 2 between the inner surface and the outer surface.

In some embodiments, the loop 6 is formed of a filament that extends distally down the inside of the body 2, out of aperture 8a and back into the body 2 through aperture 8b, and proximally back up the inside of the body 2. In such embodiments, the loop 6 may be tightened by pulling both ends of the filament in order to secure, grip, and/or compress the lead 4 against the body 2 with the loop 6 as shown in FIG. 2, for example. In other embodiments, the loop 6 is formed of a filament that is fixedly attached at one end to the body 2, with the free end extending proximally through the inside of the body 2. In such embodiments, the loop 6 may be tightened by pulling the free end of the filament in order to secure, grip, and/or compress the lead 4 against the body 2 with the loop 6, as shown in FIG. 2, for example.

Figure 3:
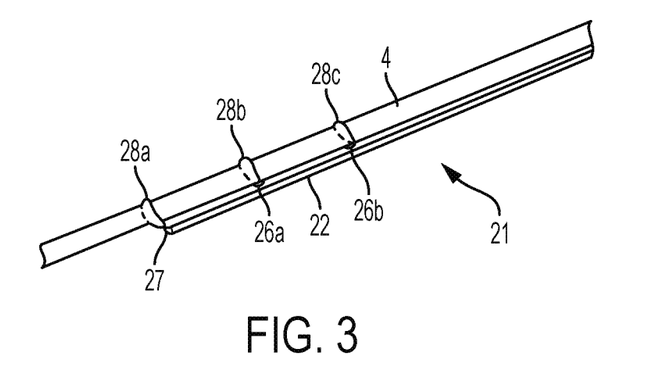
FIG. 3 illustrates a multi-loop lead extension device encircling a lead, according to another embodiment of the present disclosure.

FIG. 3 illustrates a multi-loop lead extension device 21 encircling a lead 4, according to another embodiment of the present disclosure. The device 21 may be constructed from small diameter hypotube, which may be referred to as body 22, with holes 26a, 26b cut through one wall to accommodate the wire, suture or braided filament forming the loops 28b-28c that exit the side of body 22. One loop 28a also exits the tube 22 through an opening 27 at the distal end. The loops 28a, 28b, and 28c are placed over the lead 4 to be extracted and then tightened by putting the wire or cord, out of which loops 28a-28c are made, in tension. Device 21 may have three loops 28a-28c, or one or two loops, or more than three loops. According to some embodiments, the loops 28a-28c may be placed over a sheath and deployed at any location along the length of the lead 4.

Figure 4:
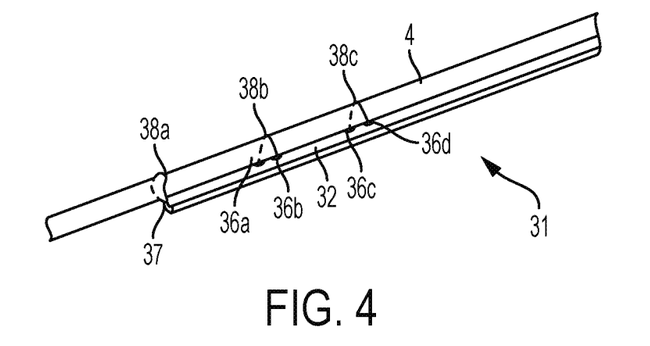
FIG. 4 illustrates a multi-loop lead extension device encircling a lead, according to another embodiment of the present disclosure.

FIG. 4 illustrates a multi-loop lead extension device 31 encircling a lead 4, according to another embodiment of the present disclosure. This illustration shows a similar device using an alternate hole configuration (holes 36a, 36b, 36c, and 36d) to support the loops 38a-38c differently when compared to device 31, which may change the amount of force used to hold the lead 4 as well as the way the filament may form into the insulation as the wire loops 38a-38c deform the lead 4. Loop 38a extends out of an opening 37 at the distal end of the body 32. Loop 38b is formed by a filament extending through holes 36a and 36b; loop 38c is formed by a filament extending through holes 36c and 36d.

Figure 5:
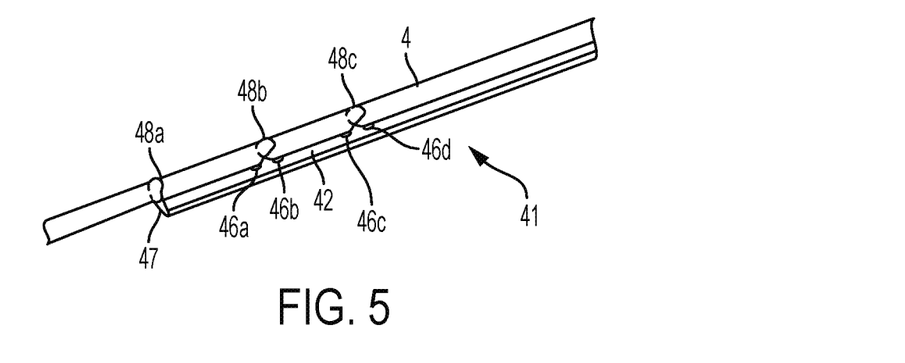
FIG. 5 illustrates a multi-loop lead extension device encircling a lead, according to another embodiment of the present disclosure.

FIG. 5 illustrates a multi-loop lead extension device 41 encircling a lead 4, according to another embodiment of the present disclosure. Device 41 is similar to devices 1, 21, and 31, but the loops 48a, 48b, and 48c include an at least half twist in them exterior of the outer surface of the body 42. Loop 48a extends out of an opening 47 at the distal end of the body 42. Loop 48b is formed by a filament extending through holes 46a and 46b; loop 48c is formed by a filament extending through holes 46c and 46d.

Figure 6:
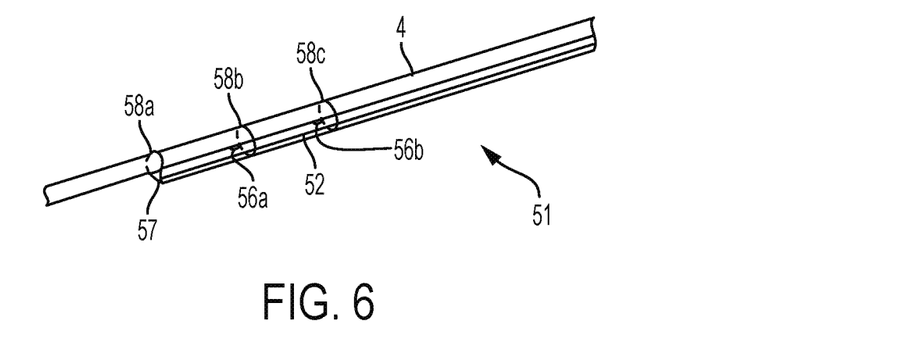
FIG. 6 illustrates a multi-loop lead extension device encircling a lead, according to another embodiment of the present disclosure.

FIG. 6 illustrates a multi-loop lead extension device 51 encircling a lead 4, according to another embodiment of the present disclosure. This illustration shows a device with yet another configuration of holes 56a, 56b. The placement of the holes 56a, 56b as well as the number of loops 58a, 58b, 58c included with the device 51 may include numerous different combinations and variations. In the embodiment of FIG. 6, each loop 58b, 58c has one leg which extends out of a respective aperture 56a, 56b, wraps all the way around the body 52 (and, when the lead 4 is inserted through the loops 58a, 58b, 58c, the lead 4) and back into the body 52 through the same respective aperture 56a, 56b. Loop 58a extends out of an opening 57 at the distal end of the body 52.

Figure 7:
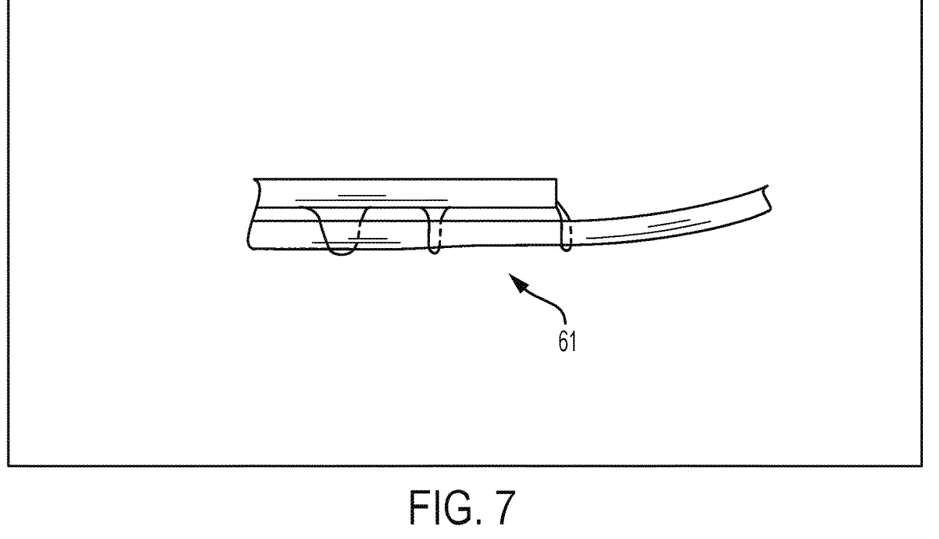
FIG. 7 illustrates a triple loop lead extension device tightened to a lead, according to another embodiment of the present disclosure.
Figure 8:
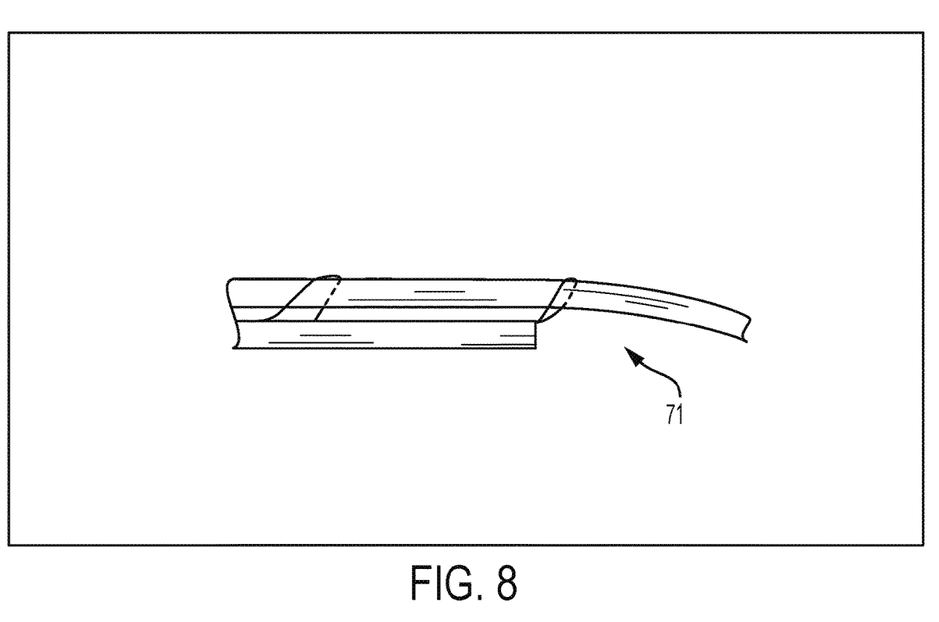
FIG. 8 illustrates a double loop lead extension device coupled to a lead, according to another embodiment of the present disclosure.
Figure 9:
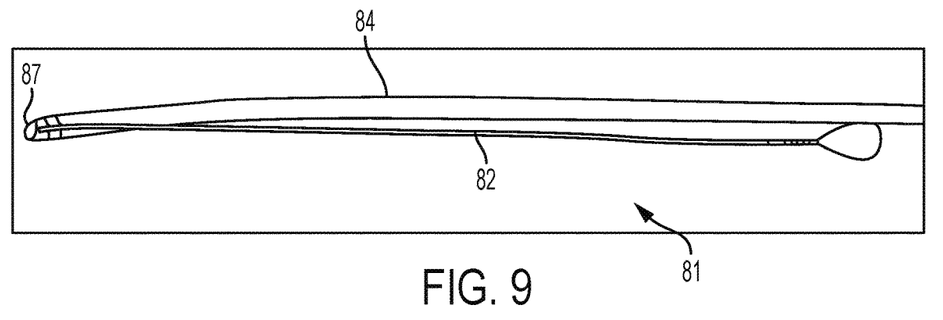
FIG. 9 illustrates a double loop lead extension device coupled to a deployment sheath, according to another embodiment of the present disclosure.
Figure 10:
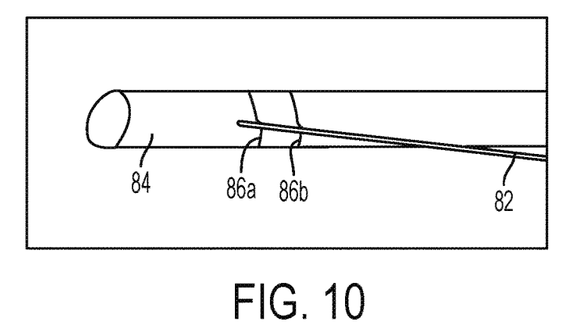
FIG. 10 illustrates an enlarged view of a distal end of the double loop lead extension device of FIG. 9 coupled to the deployment sheath, according to an embodiment of the present disclosure.
Figure 11:
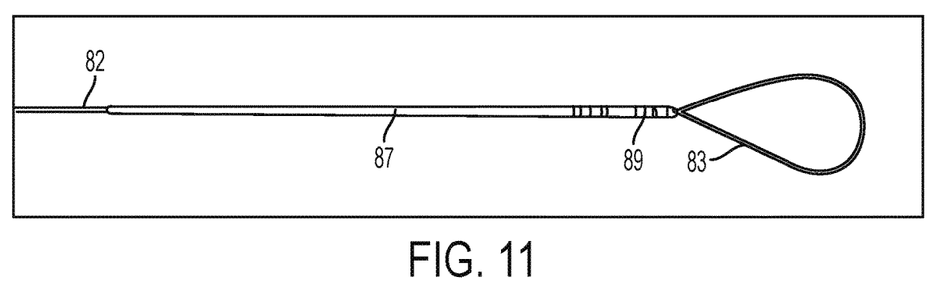
FIG. 11 illustrates a proximal end/tether of the double loop lead extension device of FIGS. 9 and 10, according to an embodiment of the present disclosure.

FIG. 7 illustrates a triple loop lead extension device 61 tightened to a lead, according to another embodiment of the present disclosure. FIG. 8 illustrates a double loop lead extension device 71 coupled to a lead, according to another embodiment of the present disclosure.

Figure 12:
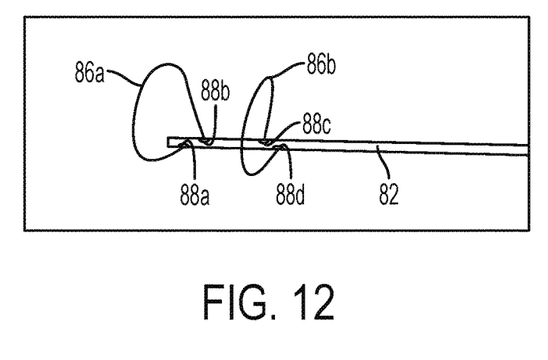
FIG. 12 illustrates an enlarged view of a distal end of the double loop lead extension device of FIGS. 9-11, prior to tightening of the double loops, according to an embodiment of the present disclosure.

FIGS. 9-12 illustrate a double loop lead extension device 81 coupled to a deployment sheath 84, according to another embodiment of the present disclosure. FIG. 12 illustrates a distal end of the device 81, showing how loops 86a, 86b are formed by one or more filaments extending from apertures 88a, 88b, 88c, and 88d formed within the body 82 of the device 81. The body 82 extends to a proximal end, shown in FIG. 11, where it terminates in a pull sleeve 87 and a pull loop 83. In some cases, the pull sleeve 87 is fixedly coupled to loop 83 by crimping mechanism 89, such that pulling loop 83 proximally causes the filament or filaments which form loops 86a, 86b to tighten by moving such filament or filaments with respect to the body 82 (for example by translating them proximally from inside the body 82). In other embodiments, the pull sleeve 87 is fixedly coupled to body 82 and the crimping mechanism 89 is used to hold loop 83 onto itself, with the crimping mechanism 89 and loop 83 being translatable proximally with respect to both the sleeve 87 and body 82. The body 82, sleeve 87, crimping mechanism 89, and/or loop 83 may be referred to as a tether or as forming part of a tether, because tension applied to them is transmitted to the loops 86a, 86b and thus to the lead to which device 81 attaches.

In order to avoid or minimize snagging or undesired deformation of the loops 86a, 86b, or to prevent unintended pull-through of the loops 86a, 86b into body 82 (for example, in embodiments in which one or more loops 86 extends from the same aperture), a deployment sheath 84 may be used to deploy the device 81 to the desired location. The loops 86a, 86b may be inserted over a distal end 87 of the deployment sheath 84 and then tightened, for example by pulling proximal loop 83. Then the deployment sheath 84 may be deployed to the desired location, for example a location next to the lead 4 to be captured or extended. Next, the loops 86a, 86b may be loosed from the deployment sheath 84, slipped off of the sheath 84, slipped over a proximal end of the lead 4, and re-tightened over the lead 4. Next, tension may be applied to the lead 4 by applying tension to the device 81, and/or a lead extraction device may be deployed over the device 81 and then the lead 4 while the lead 4 is held under tension using device 81.

Figure 13:
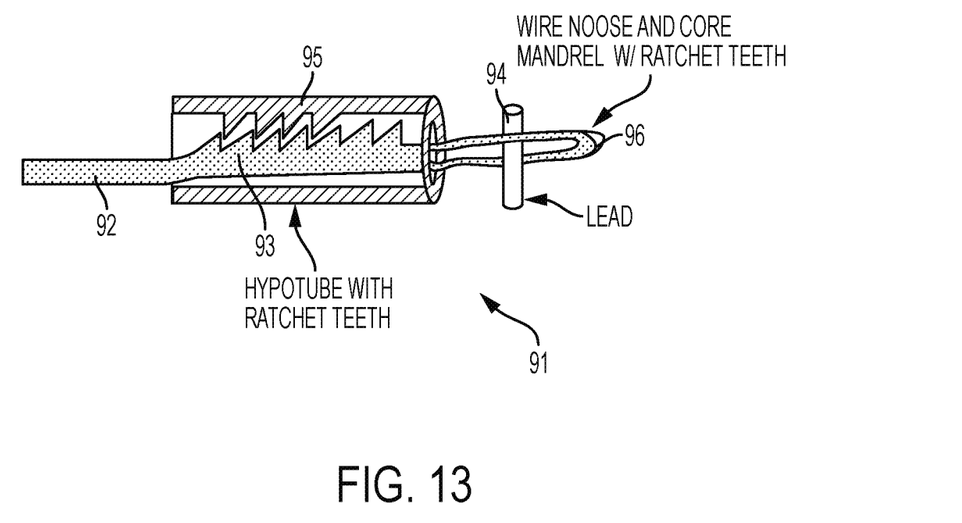
FIG. 13 illustrates a partial cross-sectional view of an alternative lead extension device, according to an embodiment of the present disclosure.

FIG. 13 illustrates a partial cross-sectional view of an alternative lead extension device 91, according to an embodiment of the present disclosure. Device 91 includes a body 92, a sleeve 95, a distal loop 96 configured to receive a lead 94 therethrough, and a ratchet-type interface formed between the portion 93 of the body 92 and an inside of the sleeve 95. According to some embodiments, once lead 94 is placed through loop 96, the sleeve 95 is advanced distally toward loop 96 and over loop 96 in order to close, squeeze, capture, and/or grip lead 94 within the loop 96 and device 91. The ratchet-type features between sleeve 95 and area 93 of body 92 permits the sleeve 95 to be slid distally with respect to body 92, but substantially inhibits movement of the sleeve 95 in a proximal direction with respect to the loop 96 and body 92, according to some embodiments.

Figure 14:
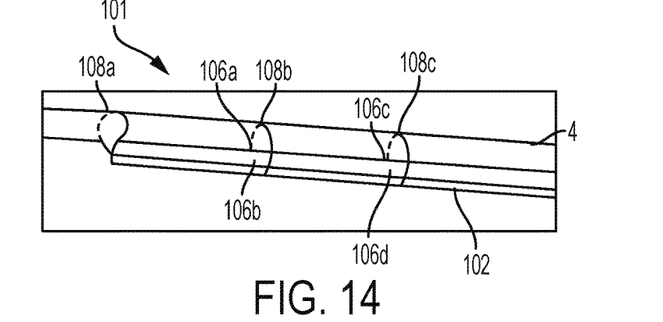
FIG. 14 illustrates a multi-loop lead extension device encircling a lead, according to another embodiment of the present disclosure.
Figure 15:
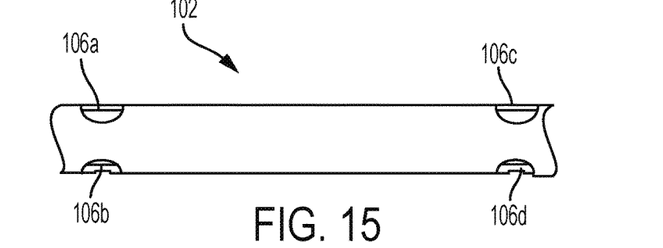
FIG. 15 illustrates a body of the multi-loop lead extension device of FIG. 14, according to an embodiment of the present disclosure.

Lead extension devices according to embodiments of the present disclosure may have various types of loop hole arrangements and orientations. For example, the loop holes may have parallel, diagonal, or offset loop hole arrangements on the body of the lead extension device. As a specific example, FIGS. 14 and 15 illustrate a multi-loop lead extension device 101 encircling a lead 4, according to another embodiment of the present disclosure. This illustration shows a device with yet another configuration of holes 106a, 106b, 106c, and 106d. The number of loops 108a, 108b, 108c included with the device 101 may be varied. In the embodiment of FIGS. 14 and 15, each loop 108b, 108c has one leg which extends out of a respective aperture 106a, 106c, wraps partially around the body 102 (and, when the lead 4 is inserted through the loops 108a, 106b, 108c, the lead 4), and back into the body 102 through a longitudinally-aligned (relative to the body 102) respective aperture 106b, 106d.

Figure 16:
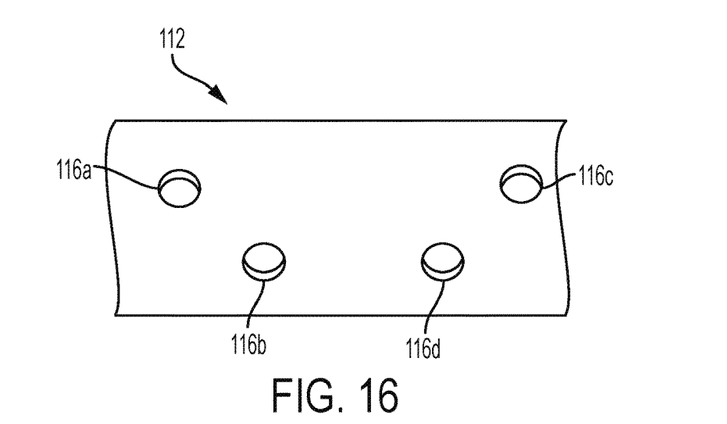
FIG. 16 illustrates a body of a multi-loop lead extension device, according to another embodiment of the present disclosure.

FIG. 16 illustrates a body 112 of a multi-loop lead extension device, according to another embodiment of the present disclosure. The body 112 may be used as, for example, the bodies 32, 42, and/or 82 described above. The body 112 includes holes 116a and 116b through which a filament extends to form a first loop (not shown). The holes 116a and 116b define a first imaginary, helically-extending line. The body 112 also includes holes 116c and 116d through which a filament extends to form a second loop (not shown). The holes 116c and 116d define a second imaginary, helically-extending line that intersects with the first imaginary, helically-extending line.

Figure 17:
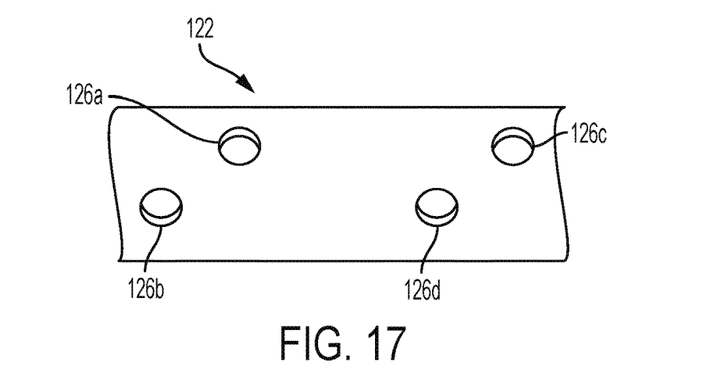
FIG. 17 illustrates a body of a multi-loop lead extension device, according to another embodiment of the present disclosure.

FIG. 17 illustrates a body 122 of a multi-loop lead extension device, according to another embodiment of the present disclosure. The body 122 may be used as, for example, the bodies 32, 42, and/or 82 described above. The body 122 includes holes 126a and 126b through which a filament extends to form a first loop (not shown). The holes 126a and 126b define a first imaginary, helically-extending line. The body 122 also includes holes 126c and 126d through which a filament extends to form a second loop (not shown). The holes 126c and 126d define a second imaginary, helically-extending line that is parallel to the first imaginary, helically-extending line.

Figure 18:
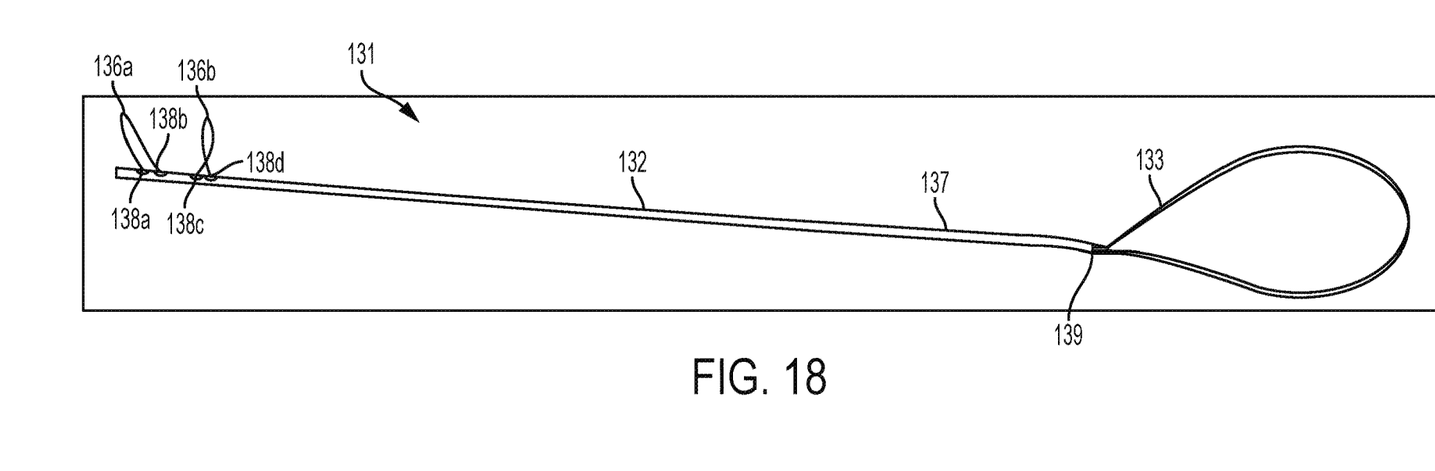
FIG. 18 illustrates a double loop lead extension device, according to another embodiment of the present disclosure.
Figure 19:
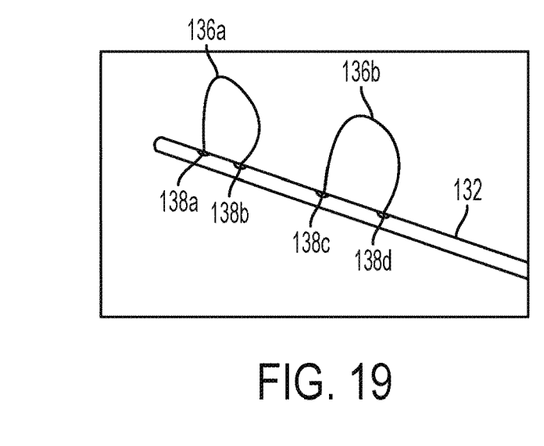
FIG. 19 illustrates an enlarged view of a distal end of the double loop lead extension device of FIG. 18, prior to tightening of the double loops, according to an embodiment of the present disclosure.

FIGS. 18-19 illustrate a double loop lead extension device 131, according to another embodiment of the present disclosure. FIG. 19 illustrates a distal end of the device 131, showing how loops 136a, 136b are formed by one or more filaments extending from apertures 138a, 138b, 138c, and 138d formed within a body 132 of the device 131. The body 132 may be or include, for example, a small diameter hypotube. The body 132 extends to a proximal end, shown in FIG. 18, where it terminates in a pull sleeve 137 and a pull loop 133. The pull sleeve 137 may be or include, for example, a small diameter hypotube that is carried on the outside of the body 132. In some cases, the pull sleeve 137 is fixedly coupled to loop 133 by crimping mechanism 139, such that pulling loop 133 proximally causes the filament or filaments which form loops 136a, 136b to tighten by moving such filament or filaments with respect to the body 132 (for example by translating them proximally from inside the body 132). In other embodiments, the pull sleeve 137 is fixedly coupled to body 132 and the crimping mechanism 139 is used to hold loop 133 onto itself, with the crimping mechanism 139 and loop 133 being translatable proximally with respect to both the sleeve 137 and body 132. The body 132, sleeve 137, crimping mechanism 139, and/or loop 133 may be referred to as a tether or as forming part of a tether, because tension applied to them is transmitted to the loops 136a, 136b and thus to the lead to which device 131 attaches.

During lead extraction procedures, traction is applied to the lead in order to assist in freeing the lead from adhesion sites. Embodiments of the present disclosure decrease the time used to deploy a lead traction or extension device during an extraction procedure. Some embodiments of the present disclosure are reversible and/or removable.

In some embodiments of the present disclosure, a thin-walled hypotube has holes toward the distal portion drilled or laser cut in various patterns which can allow a braided wire, nitinol wire with pre-shaped loops, suture, oval wire, oval nitinol wire, or braided suture, to pass down the inner diameter and form loops at the distal end. During a lead removal procedure, the loops are positioned over the lead body and/or the high voltage cables. By pulling on the wire or wires, the loops close and pull the lead or cables tightly against the hypotube body. Traction may then be applied to such device in order to pull the lead and/or lead cables to which the device is attached. If removal of the traction device is desired, the wire, braided wires, suture, braided suture or nitinol loops may be released or made slack, with the outer cannula or shaft being tugged and the loops released, for example. In some embodiments, the tip of the lead extension devices described herein may be atraumatic to aide in its deployment, so as not to perforate or damage target anatomy.

The lead extension devices described herein may also be long enough and flexible enough to be placed in the vasculature in order to grasp a lead at any location along its length or grasp a lead that has been previously broken. The lead extension devices described herein may also be sufficiently long to extend through lead extraction devices. Such devices may also be used to grasp a pacemaker or implantable cardioverter defibrillator tip that may have broken loose from a lead body.

According to some embodiments, the pull wire(s), nitinol loops, braids, and the like, can be one continuous cord to close all loops simultaneously, or can have all separate cords to pull each loop closed as desired. A sleeve or sleeves may be attached to the cables, wires, braids, and/or nitinol loops, to aide in pulling the loops closed or otherwise tightening the loops. Such a pull sleeve could use a variety of locking mechanisms including but not limited to friction, lock tabs, ratchets, locking detents, cam paths, twisting/screw mechanisms, and the like.

A pull wire or wire with a loop or loops may also be attached to the lead extension devices described herein, in order to facilitate the threading of such devices through a lead extraction device. Many different materials may be used to construct the lead extension devices described herein and/or their components, including but not limited to stainless steel, nitinol, polymers (such as Pebae), fibers, and other materials. According to some embodiments, the body of the lead extension devices disclosed herein may include a first, relatively rigid material near the distal end of the body (that is, the portion of the body that defines the loop holes and engages a lead to be extracted) and a second, relatively flexible material for the remainder of the body (to facilitate placement in the vasculature). According to some embodiments, the body of the lead extension devices disclosed herein may have a relatively rough surface (by applying a surface treatment or the like) near the distal end of the body to facilitate engaging a lead to be extracted. The positioning and/or the shape of the apertures formed in the bodies of the lead extraction devices described herein may be selected to enhance an ability to tighten or otherwise pull the loops closed, as well as to aide in the opening of the loops when release or reversal is desired.

In the appended figures, similar components and/or features may have the same reference label. Further, various components of the same type may be distinguished by following the reference label by a letter that distinguishes among the similar components. If only the first reference label is used in the specification, the description is applicable to any one of the similar components having the same first reference label irrespective of the second reference label.

A number of variations and modifications of the disclosure may be used. It would be possible to provide for some features of the disclosure without providing others.

For example, while devices are described above as being able to attach to leads 4 and/or deployment sheaths 84, such devices may also be used to attach to insulation portions of leads and/or high voltage wires or other components of leads or other elongated elements.

The present disclosure, in various aspects, embodiments, and/or configurations, includes components, methods, processes, systems and/or apparatus substantially as depicted and described herein, including various aspects, embodiments, configurations embodiments, sub combinations, and/or subsets thereof. Those of skill in the art will understand how to make and use the disclosed aspects, embodiments, and/or configurations after understanding the present disclosure. The present disclosure, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving ease and/or reducing cost of implementation.

The foregoing discussion has been presented for purposes of illustration and description. The foregoing is not intended to limit the disclosure to the form or forms disclosed herein. In the foregoing Summary for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Summary, with each claim standing on its own as a separate embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A device for extending a lead, comprising:
an elongate body having a longitudinal axis and a circumference,
wherein the elongate body includes a lumen and a wall, the wall including a first aperture, a second aperture, a third aperture, and a fourth aperture, the second aperture being distally positioned relative to the first aperture, the third aperture being distally positioned relative to the second aperture, the fourth aperture being distally positioned relative to the third aperture,
wherein the first aperture and the second aperture are offset along the longitudinal axis and offset along the circumference, wherein the first aperture and the third aperture are offset along the longitudinal axis and offset along the circumference,
wherein the second aperture and the fourth aperture are offset along the longitudinal axis and offset along the circumference,
wherein the third aperture and the fourth aperture are offset along the longitudinal axis and offset along the circumference;
a filament comprising:
a first filament loop extending along the lumen and through the first aperture and the second aperture; and
a second filament loop extending along the lumen and through the third aperture and the fourth aperture;
wherein the first and second filament loops are arranged to receive a lead.

2. The device of claim 1, wherein the elongate body is tubular and includes an opening at a distal end of the elongate body, wherein the filament further comprises a third filament loop, and wherein the third filament loop extends through the opening.

3. The device of claim 1, further comprising a third filament loop extending outside the outer surface of the elongate body, the first, second, and third filament loops arranged to receive therethrough the lead, the first, second, and third filament loops being tightenable about the lead to grip at least a portion of the outer surface of the lead against the elongate body.

4. The device of claim 1, wherein the filament is of a construct selected from the group consisting of monofilament wire, multifilament wire, monofilament suture, multifilament suture, and braided strands.

5. The device of claim 1, wherein each of the first and second filament loops comprise at least a half twist outside the outer surface of the elongate body.

6. The device of claim 1, wherein the filament is fixedly coupled to the elongate body on one side of the first filament loop.

7. The device of claim 1, wherein the filament further comprises an end coupled to the elongate body.

8. The device of claim 7, wherein the end of the filament is fixedly attached to the elongate body.

9. The device of claim 1, wherein the first and second filament loops are configured to simultaneously tighten about the lead to grip at least a portion of the lead against the elongate body.

10. The device of claim 1, further comprising a means for transferring a tension force to the lead.

11. The device of claim 10 wherein the means for transferring a tension force to the lead comprises the elongate body and at least one of the first filament loop or the second filament loop.

12. The device of claim 11 wherein the means for transferring a tension force to the lead comprises the elongate body, the first filament loop, and the second filament loop.

13. The device of claim 11, wherein the means for transferring a tension force to the lead comprises a tether.

* * * * *